(12) United States Patent
Miyamoto et al.

(10) Patent No.: US 6,258,254 B1
(45) Date of Patent: *Jul. 10, 2001

(54) BIOSENSOR

(75) Inventors: Yoshiko Miyamoto, Suita; Shin Ikeda, Katano; Toshihiko Yoshioka; Shiro Nankai, both of Hirakata, all of (JP)

(73) Assignee: Matsushita Electric Industrial Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/122,628

(22) Filed: Jul. 27, 1998

(30) Foreign Application Priority Data

Jul. 28, 1997 (JP) .................................................. 9-201620

(51) Int. Cl.$^7$ ........................................................ G01F 1/64
(52) U.S. Cl. ........................................ 205/777.5; 204/403
(58) Field of Search ........................ 204/403; 205/777.5, 205/778; 435/287.9, 4, 817

(56) References Cited

U.S. PATENT DOCUMENTS

| | | |
|---|---|---|
| 4,743,352 | 5/1988 | Watkins-Pitchford . |
| 4,810,640 * | 3/1989 | Nakamura et al. ..................... 435/25 |
| 4,981,572 | 1/1991 | Easmunt et al. . |
| 5,368,712 | 11/1994 | Tomich et al. . |
| 5,543,024 | 8/1996 | Hanazato et al. . |
| 5,582,697 * | 12/1996 | Ikeda et al. ........................... 204/403 |
| 5,651,869 * | 7/1997 | Yoshioka et al. ..................... 204/403 |
| 5,658,443 * | 8/1997 | Yamamoto et al. .................. 204/403 |
| 5,658,444 | 8/1997 | Black et al. . |
| 5,720,862 * | 2/1998 | Hamamoto et al. .................. 204/403 |
| 5,746,898 * | 5/1998 | Preidel ................................. 204/403 |
| 5,798,031 * | 8/1998 | Charlton et al. ..................... 204/403 |

FOREIGN PATENT DOCUMENTS

| | | | |
|---|---|---|---|
| 0094677 | 5/1983 | (EP) . | |
| 0136362 | 3/1984 | (EP) . | |
| 177743 A2 * | 4/1986 | (EP) | ................................. 435/287.9 |
| 62-172255 | 7/1987 | (JP) . | |
| 63-230078 | 9/1988 | (JP) . | |
| 01023153 | 1/1989 | (JP) . | |
| 64-23153 * | 1/1989 | (JP) | ..................................... 204/403 |
| 64-59056 * | 3/1989 | (JP) | ..................................... 204/403 |
| 1-114747 * | 5/1989 | (JP) | ..................................... 204/403 |
| 01153952 | 6/1989 | (JP) . | |
| 2-62952 * | 3/1990 | (JP) | ..................................... 204/403 |
| 2-157645 * | 6/1990 | (JP) | ..................................... 204/403 |
| 02228548 | 11/1990 | (JP) . | |
| 03202764 | 9/1991 | (JP) . | |
| 03160358 | 10/1991 | (JP) . | |
| 5-256812 * | 10/1993 | (JP) | ..................................... 204/403 |
| 6-88804 * | 3/1994 | (JP) | ..................................... 204/403 |
| 07083872 | 3/1995 | (JP) . | |

* cited by examiner

*Primary Examiner*—Robert J. Warden, Sr.
*Assistant Examiner*—Andrew Aldag
(74) *Attorney, Agent, or Firm*—McDermott, Will & Emery

(57) ABSTRACT

A method using a biosensor is disclosed which facilitates high accuracy quantitation of a substrate by best eliminating adverse effects of red blood cell existing in blood together with the substrate. The biosensor comprises an electrode system including a working electrode and a counter electrode formed on an electrically insulating base plate, and a reaction layer containing at least an oxidoreductase and an electron acceptor, wherein the electron acceptor is a sodium salt.

3 Claims, 2 Drawing Sheets

BIOSENSOR

BACKGROUND OF THE INVENTION

The present invention relates to a biosensor for quantitating a specific component contained in a sample collected from a body.

Conventionally, a biosensor has been disclosed in Japanese Laid-Open Patent Publication Hei 3-202764 as a system for facilitating simple quantitation of a specific component in a sample with no need of dilution or agitation of a sample solution.

This conventional biosensor is produced by forming an electrode system having a working electrode and a counter electrode on an electrically insulating base plate by a screen printing method or the like and subsequently forming an enzyme reaction layer including a hydrophilic polymer, an oxidoreductase and an electron acceptor above the electrode system.

When the biosensor thus produced is added with a drop of a sample solution containing a substrate over the enzyme reaction layer, the enzyme reaction layer is dissolved in the sample solution. As a result, reaction between the substrate in the sample solution and the enzyme in the enzyme reaction layer will take place, which in turn causes oxidation of the substrate and reduction of the electron acceptor. Upon completion of enzyme reaction, the reduced electron acceptor is oxidized electrochemically. The concentration of the substrate in the sample solution can be quantitated based on the oxidation current value measured during this oxidizing process.

Such biosensor can quantitate various substrates if an adequate oxidoreductase fit for the measuring substrate is adopted.

Here, a glucose sensor will be described as an example of biosensor.

Conventionally known method for electrochemical quantitative measurement of glucose is a system comprising a combination of glucose oxidase (EC1.1.3.4) with an oxygen electrode or a hydrogen peroxide electrode (e.g., "Biosensor", ed. by Shuichi Suzuki, Kodansha, Japan). to D-glucono-δ-lactone by utilizing oxygen as an electron acceptor. In association with this oxidation reaction, the electron acceptor oxygen is reduced to hydrogen peroxide. Glucose concentration can be quantitated either by measurement of the oxygen consumption volume during this reaction using an oxygen electrode or by measurement of the produced amount of hydrogen peroxide using a hydrogen peroxide electrode.

However, this method has a drawback that the measurement is largely affected by the concentration of the oxygen contained in a sample solution, depending on the measuring material. This system has another drawback that the system can not function as a biosensor in an environment lacking oxygen.

To overcome these problems, a glucose sensor of a new type has been developed which includes an organic compound or a metal complex such as ferricyanides, ferrocene derivatives, quinone derivatives, etc. as electron acceptor, in place of oxygen.

This biosensor can carry a known amount of glucose oxidase on an electrode system, together with an electron acceptor in their stabilized state. As a result, the electrode system can be integrated with the reaction layer almost in dry state.

Such biosensor is normally disposable and facilitates measurement of the concentration of a substrate (glucose in this case) by a simple instillation of a measuring sample in a sensor chip mounted in a measurement device. Therefore, this biosensor has been attracting much attention recently and is widely applied effectively in determining diagnostic guidelines at various medical facilities.

As shown above, with this conventional biosensor, the electron acceptor present in the reaction layer is an organic compound or a metal complex such as ferricyanides, ferrocene derivatives, quinone derivatives, etc. and particularly preferred is a potassium salt.

However, the presence of potassium ions exceeding physiological level has an adverse effect on the condition of red blood cell (RBC), leading to a collapse of RBC. Such event impairs the response of the sensor to a blood sample. Therefore, it is sometimes observed that the sensor response varied depending on the number of RBCs in the blood sample, even if the substrate concentration in the blood is the same.

BRIEF SUMMARY OF THE INVENTION

The object of the present invention is to provide a biosensor which can best eliminate the adverse influence of RBC present in blood together with a substrate, thereby facilitating high accuracy quantitation of the substrate.

The present invention provides a biosensor comprising an electrode system including a working electrode and a counter electrode formed on an electrically insulating base plate, and a reaction layer containing at least an oxidoreductase and an electron acceptor, wherein the electron acceptor is a sodium salt.

In a preferred mode of the present invention, the sodium salt is sodium ferricyanide.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

Sodium ions produced by dissolution of a sodium salt in a sample solution have less influence on the morphological change of RBC in blood. This means that the use of a sodium salt for electron acceptor best eliminates the effect of the difference of RBC content in blood on the sensor response.

Such sodium salt may be exemplified as sodium ferricyanide, sodium β-naphthoquinone-4-sulfonate, and the like.

The biosensor in accordance with the present invention is applicable to the quantitative measurement of any component contained in blood. The usable oxidoreductase for the biosensor, therefore, includes glucose oxidase, glucose dehydrogenase, alcohol oxidase, alcohol dehydrogenase, cholesterol oxidase, cholesterol dehydrogenase, lactate oxidase, lactate dehydrogenase, ascorbate oxidase, bilirubin oxidase, and the like.

By selecting one from the above-exemplified oxidoreductases, a glucose sensor, an alcohol sensor, a cholesterol sensor, a lactate sensor, an ascorbate sensor, a bilirubin sensor, etc. can be produced with the biosensor in accordance with the present invention.

It is preferred from the aspect of protection of the surface of the electrode system formed on the base plate from the enzyme and electron acceptor to cover the electrode system with a hydrophilic polymer.

The hydrophilic polymer used for this purpose is at least one selected from the group consisting of carboxymethyl cellulose, hydroxyethyl cellulose, hydroxypropyl cellulose, carboxyethylmethyl cellulose, polyvinyl pyrrolidone, polyvinyl alcohol, gelatin and its derivative, a polymer of acrylic acid or an acrylate, a polymer of methacrylic acid or a methacrylate, starch and its derivative, a polymer of maleic anhydride or a maleate.

The system for measuring the oxidation current value includes a two-electrode system comprising a working electrode and a counter electrode and a three-electrode system further comprising a reference electrode. The latter can produce more accurate measurement results. In the following, the present invention will be described more specifically by way of concrete examples.

Figure 1:
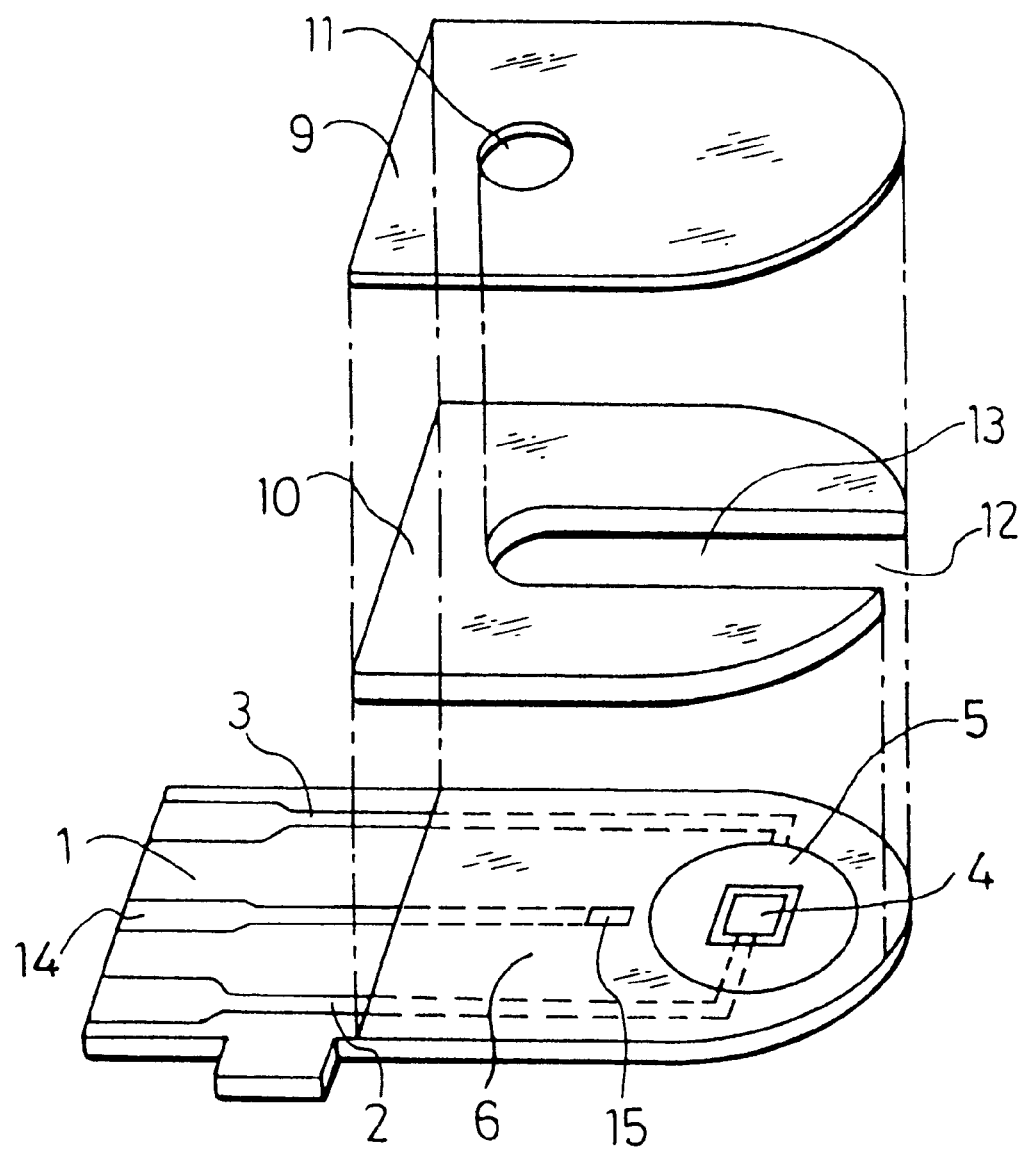
FIG. 1 is an exploded perspective view of a biosensor in accordance with one example of the present invention, from which the reaction layer has been omitted.

FIG. 1 shows an exploded perspective view of a biosensor in accordance with the present invention with an omission of the reaction layer.

As shown in FIG. 1, a silver paste is printed on an electrically insulating base plate 1 of polyethylene terephthalate by the screen printing method so as to form leads 2 and 3 on the base plate 1. Subsequently, a conductive carbon paste containing a resin binder is printed on the base plate 1 so as to form a working electrode 4. The working electrode 4 is in contact with the lead 2. Then, an electrically insulating layer 6 is further formed on the base plate 1 by printing thereon an insulating paste. The electrically insulating layer 6 covers the periphery of the working electrode 4 so as to hold the exposed area of the working electrode 4 constant. Thereafter, a conductive carbon paste containing a resin binder is printed on the base plate 1 so as to cause the carbon paste to contact the previously formed lead 3, which formed a ring-like counter electrode 5.

Then, a reaction layer is formed on or in the vicinity of the electrode system comprising the working electrode and the counter electrode. The electrically insulating base plate 1 having thereon the reaction layer, a cover 9 having an air vent 11 and a spacer 10 are bonded to each other in a positional relationship as shown by the dotted chain line in FIG. 1, which gives a biosensor of the present invention. The spacer 10 has a slit 13 for forming a sample supply path between the base plate and the cover. Numeral 12 corresponds to an opening of the sample supply path.

Figure 2:
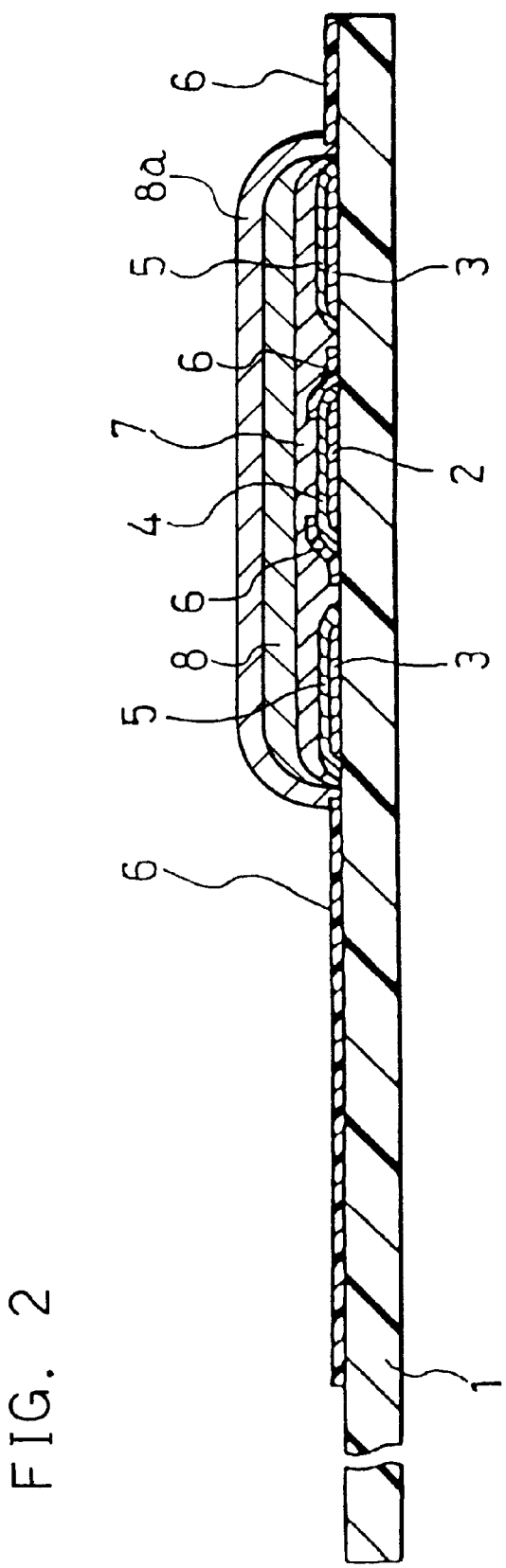
FIG. 2 is a longitudinal cross-sectional view of the vital part of the biosensor.

FIG. 2 shows the longitudinal cross-section of the vital part of a biosensor embodied in one example of the present invention, from which the spacer and the cover have been omitted.

The electrically insulating base plate 1 above which the electrode system has been formed as shown in FIG. 1 is further formed thereon with a hydrophilic polymer layer 7, an enzyme-containing layer or a reaction layer 8 containing an enzyme and an electron acceptor, and a lecithin layer 8a.

EXAMPLE 1

In this example, an aqueous solution of carboxymethyl cellulose (hereinafter referred to as "CMC") was dropped on the electrode system formed above the base plate 1 in FIG. 1 and dried for 10 min in a hot drier at 50° C. so as to form the CMC layer 7. Then, a mixed aqueous solution was formulated by dissolving 200 units of glucose oxidase and 40 μmol of sodium ferricyanide in 1 ml of water. The resultant mixed aqueous solution (5 μl) was dropped on the previously formed CMC layer 7 and dried for 10 min in a hot drier at 50° C. similarly so as to form the reaction layer 8 containing an oxidoreductase (glucose oxidase) and an electron acceptor (sodium ferricyanide).

Then, a toluene solution of lecithin was further dropped above the reaction layer 8 and dried to form the lecithin layer 8a. After formation of those layers on the base plate 1, the cover 9 and the spacer 10 were bonded to the base plate 1 in a positional relationship shown by the dotted chain line in FIG. 1. In this way, a glucose sensor of this example was produced.

Blood samples containing 300 mg/dl glucose and having an RBC volume ratio (hematocrit reading) of 0%, 25%, 38% and 50% were formulated and used as the sample solutions for the glucose sensor. The blood sample of hematocrit 0% represents plasma.

When 3 μl of the plasma sample solution was supplied from the opening 12 of the sample supply path, the sample solution advanced up to the air vent 11 and dissolved the CMC layer 7, the reaction layer 8 and the lecithin layer 8a present above the electrode system. Twenty-five seconds after supply of the sample solution, a constant voltage of +0.5 V was applied to the working electrode 4 using the counter electrode 5 of the electrode system as reference, and the current value was measured 5 seconds after voltage application.

The current values for the sample solutions having a hematocrit reading of 25%, 38% and 50% were determined in the same manner as shown above.

The responsive current value of the glucose sensor was constant irrespective of the hematocrit value of the sample.

Comparative Example 1

The CMC layer 7 was formed on the electrode system in FIG. 1 in the same manner as in Example 1. Then, another mixed aqueous solution was formulated by dissolving 200 units of glucose oxidase and 40 μmol of potassium ferricyanide in 1 ml of water. The resultant mixed aqueous solution (5 μl) was dropped on the previously formed CMC layer 7 and dried for 10 min in a hot drier at 50° C. so as to form the reaction layer 8 containing an oxidoreductase (glucose oxidase) and an electron acceptor (potassium ferricyanide).

Then, the lecithin layer 8a was formed above the reaction layer in the same manner as in Example 1, which gave a glucose sensor of Comparative Example 1. The glucose sensor was evaluated for its response characteristic in the same manner as in Example 1.

The responsive current value decreased with the increase of hematocrit reading. The ratio of the responsive current value is shown in Table 1. In the table, the responsive current value of the sensor to plasma (hematocrit 0%) was defined as 100%.

TABLE 1

| Hematocrit value (%) | Ratio |
|---|---|
| 0 | 100 |
| 25 | 90 |
| 38 | 85 |
| 50 | 80 |

EXAMPLE 2

The CMC layer 7 was formed on the electrode system in FIG. 1 in the same manner as in Example 1. Then, another mixed aqueous solution was formulated by dissolving 400 units of lactate oxidase and 40 μmol of sodium ferricyanide in 1 ml of water. The resultant mixed aqueous solution (5 μl) was dropped on the previously formed CMC layer 7 and dried for 10 min in a hot drier at 50° C. so as to form the reaction layer 8 containing an oxidoreductase (lactate oxidase) and an electron acceptor (sodium ferricyanide).

Then, the lecithin layer 8a was formed above the reaction layer in the same manner as in Example 1, which gave a lactate sensor of Example 2.

Blood samples containing 50 mg/dl lactic acid and having a hematocrit reading of 0%, 25%, 38% and 50% were formulated and used as the sample solutions for the lactate sensor. The blood sample of hematocrit 0% represents plasma.

The lactate sensor was evaluated for its response characteristic in the same manner as in Example 1. The results showed constant responsive current values of the lactate sensor irrespective of the hematocrit level.

Comparative Example 2

The CMC layer 7 was formed on the electrode system in FIG. 1 in the same manner as in Example 1. Then, another mixed aqueous solution was formulated by dissolving 400 units of lactate oxidase and 40 μmol of potassium ferricyanide in 1 ml of water. The resultant mixed aqueous solution (5 μl) was dropped on the previously formed CMC layer 7 and dried for 10 min in a hot drier at 50° C. so as to form the reaction layer 8 containing an oxidoreductase (lactate oxidase) and an electron acceptor (potassium ferricyanide).

Then, the lecithin layer 8a was formed above the reaction layer in the same manner as in Example 1, which gave a lactate sensor of Comparative Example 2. The lactate sensor was evaluated for its response characteristic in the same manner as in Example 2.

The result showed that the responsive current value of the lactate sensor decreased with the increases of hematocrit reading. The ratio of the responsive current value is shown in Table 2. In the table, the responsive current value of the sensor to plasma (hematocrit 0%) was defined as 100%.

TABLE 2

| Hematocrit value (%) | Ratio |
|---|---|
| 0 | 100 |
| 25 | 95 |
| 38 | 90 |
| 50 | 86 |

As discussed above, the present invention can provide a biosensor facilitating high accuracy quantitation of a substrate with no adverse influence of other blood component than the substrate in blood.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

We claim:

1. A method for measuring a component in whole blood comprising:
    applying said whole blood to an electrode system, said electrode system including a working electrode and a counter electrode formed on an electrically insulating base plate,
    applying a voltage to said working electrode, and
    allowing said component in said whole blood to react with a reaction layer, said reaction layer containing at least an oxidoreductase and an electron acceptor, wherein said electron acceptor is a sodium salt, and wherein said sodium salt facilitates measurement of said component in said whole blood without adversely affecting erythrocytes in said whole blood.

2. A method in accordance with claim 1, wherein said sodium salt is sodium ferricyanide.

3. A method in accordance with claim 1, wherein said reaction layer further contains a hydrophilic polymer.

* * * * *